United States Patent
Spodsberg et al.

(10) Patent No.: US 10,010,094 B2
(45) Date of Patent: *Jul. 3, 2018

(54) POLYPEPTIDES HAVING BETA-1,3-GALACTANASE ACTIVITY AND POLYNUCLEOTIDES ENCODING SAME

(71) Applicant: Novozymes A/S, Bagsvaerd (DK)

(72) Inventors: Nikolaj Spodsberg, Bagsvaerd (DK); Kristian Bertel Roemer M Krogh, Bagsvaerd (DK); Rune Nygaard Monrad, Hilleroed (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/909,579

(22) PCT Filed: Aug. 15, 2014

(86) PCT No.: PCT/EP2014/067505
§ 371 (c)(1),
(2) Date: Feb. 2, 2016

(87) PCT Pub. No.: WO2015/022429
PCT Pub. Date: Feb. 19, 2015

(65) Prior Publication Data
US 2016/0174589 A1    Jun. 23, 2016

(30) Foreign Application Priority Data
Aug. 15, 2013   (EP) .................... 13180579

(51) Int. Cl.
| | |
|---|---|
| A23F 5/24 | (2006.01) |
| A23F 5/28 | (2006.01) |
| C12N 9/38 | (2006.01) |
| C12N 9/24 | (2006.01) |
| C12N 15/15 | (2006.01) |
| C12N 1/21 | (2006.01) |

(52) U.S. Cl.
CPC ............. *A23F 5/246* (2013.01); *A23F 5/28* (2013.01); *C12N 9/2468* (2013.01); *C12Y 302/01181* (2015.07)

(58) Field of Classification Search
None
See application file for complete search history.

(56) References Cited

PUBLICATIONS

Wahl et al., Molecular hybridization of immobilized nucleic acids: theoretical concepts and practical considerations, Methods Enz., 1987, 152, 399-07.*
Floudas et al., The Paleozoic Origin of Enzymatic Lignin Decomposition Reconstructed from 31 Fungal Genomes, Science, Jun. 2012, 336, 1715-19 and supplemental materials.*
Binder et al., *Amylocorticiales* ord. nov. and *Jaapiales* ord. nov.: Early diverging clades of Agaricomycetidae dominated by corticioid forms, Mycologia, 2010, 102, 865-80.*
Floudas et al, 2013, Uniport No. R7RZP9.
Floudas et al, 2014, XP055148713.
Kotake et al, 2009, Biosci Biotech Biochem, vol. 73, No. 10, pp. 2303-2309.
Kotake et al, 2011, J Biolo Chem, vol. 286, No. 31, pp. 27848-27854.
Strohmeier et al, 2004, Protein Sci, vol. 13, No. 12, pp. 3200-3213.

* cited by examiner

*Primary Examiner* — Tekchand Saidha
*Assistant Examiner* — Todd M Epstein
(74) *Attorney, Agent, or Firm* — Elias Lambiris

(57) ABSTRACT

The present invention relates to polypeptides having beta-1,3-galactanase activity and polynucleotides encoding the polypeptides. The invention also relates to nucleic acid constructs, vectors, and host cells comprising the polynucleotides as well as methods of producing and using the polypeptides.

6 Claims, No Drawings

POLYPEPTIDES HAVING BETA-1,3-GALACTANASE ACTIVITY AND POLYNUCLEOTIDES ENCODING SAME

CROSS-REFERENCE TO RELATED APPLICATIONS

This application is a 35 U.S.C. 371 national application of PCT/EP2014/067505 filed Aug. 15, 2014, which claims priority or the benefit under 35 U.S.C. 119 of European application no. 13180579.8 filed Aug. 15, 2013 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having beta-1,3-galactanase activity and polynucleotides encoding the polypeptides. The invention also relates to nucleic acid constructs, vectors, and host cells comprising the polynucleotides as well as methods of producing and using the polypeptides.

Description of the Related Art

Cloning and expression in *Pichia pastoris* of exo-beta-1,3-galactanase from *Irpex lacteus* has been described in Kotake et al. (2009), *Biosci. Biotech. Biochem.*, 73:2303-2309.

It is an object of the invention to provide polypeptides having beta-1,3-galactanase activity. It is a further object to provide polypeptides which are useful in selective and efficient solubilisation of carbohydrates from coffee.

The present invention provides polypeptides having beta-1,3-galactanase activity and polynucleotides encoding the polypeptides.

SUMMARY OF THE INVENTION

The present invention relates to polypeptides having beta-1,3-galactanase activity selected from the group consisting of:

(a) a polypeptide having at least 65% sequence identity to the mature polypeptide of SEQ ID NO: 2;

(b) a polypeptide encoded by a polynucleotide that hybridizes under low stringency conditions with the mature polypeptide coding sequence of SEQ ID NO: 1 or the full-length complement hereof;

(c) a polypeptide encoded by a polynucleotide having at least 65% sequence identity to the mature polypeptide coding sequence of SEQ ID NO: 1;

(d) a variant of the mature polypeptide of SEQ ID NO: 2 comprising a substitution, deletion, and/or insertion at one or more positions; and (e) a fragment of the polypeptide of (a), (b), (c), or (d) that has beta-1,3-galactanase activity.

Preferably, the polypeptide is an isolated polypeptide.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to use of the polypeptides in coffee extraction.

The present invention also relates to a polynucleotide encoding a signal peptide comprising or consisting of amino acids 1 to 20 of SEQ ID NO: 2 which is operably linked to a gene encoding a protein; nucleic acid constructs, expression vectors, and recombinant host cells comprising the polynucleotides; and methods of producing a protein.

Definitions

Beta-1,3-galactanase: The term "beta-1,3-galactanase" or "enzyme having beta-1,3-galactanase activity" means an enzyme which specifically hydrolyses beta-1,3-galactan and beta-1,3-galactooligosaccharides. The enzyme may be categorized as EC 3.2.1.181. The enzyme may have primarily endo-beta-1,3-galactanase activity. For purposes of the present invention, beta-1,3-galactanase activity is determined according to the procedures described in the Examples. In one aspect, a beta-1,3-galactanase according to the present invention has at least 20%, e.g., at least 40%, at least 50%, at least 60%, at least 70%, at least 80%, at least 90%, at least 95%, or at least 100% of the beta-1,3-galactanase activity of the mature polypeptide of SEQ ID NO: 2. The beta-1,3-galactanase activity may be quantified using the Reducing sugar assay (PAH-BAH assay) described in Example 6 with Smith degraded Gum Arabic or Acid treated Gum Arabic as substrate.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has beta-1,3-galactanase activity. In one aspect, a fragment contains at least 200 amino acid residues, at least 210 amino acid residues, or at least 225 amino acid residues.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N terminal processing, C terminal truncation, glycosylation, phosphorylation, etc. In one embodiment, the mature polypeptide of SEQ ID NO: 2 is amino acids 21 to 256 of SEQ ID NO: 2 based on the SignalP program (Nielsen et al., 1997, *Protein Engineering* 10: 1-6) predicting a signal peptide of 20 residues. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having beta-1,3-galactanase activity. In one aspect, the mature polypeptide coding sequence is nucleotides 61 to 771 of SEQ ID NO: 1 (including the stop codon) based on the SignalP program (Nielsen et al., 1997, supra) program that predicts nucleotides 1 to 60 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-1,3-galactanase activity. In one aspect, a subsequence contains at least 600 nucleotides, at least 630 nucleotides, or at least 675 nucleotides.

Variant: The term "variant" means a polypeptide having beta-1,3-galactanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g., several) amino acids, e.g., 1-5 amino acids, adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION OF THE INVENTION

Polypeptides Having Beta-1,3-galactanase Activity

In an embodiment, the present invention relates to polypeptides having a sequence identity to SEQ ID NO: 2 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have beta-1,3-galactanase activity. In one aspect, the polypeptides differ by up to 10 amino acids, e.g., 1, 2, 3, 4, 5, 6, 7, 8, 9, or 10, from the polypeptide of SEQ ID NO: 2.

In an embodiment, the present invention relates to polypeptides having a sequence identity to amino acids 21 to 256 of the polypeptide of SEQ ID NO: 2 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have beta-1,3-galactanase activity. In one aspect, the polypeptides differ by up to 10 amino acids, e.g., 1, 2, 3, 4, 5, 6, 7, 8, 9, or 10, from amino acids 21 to 256 of the polypeptide of SEQ ID NO: 2.

In another embodiment, the present invention relates to polypeptides having a sequence identity to the mature polypeptide of SEQ ID NO: 2 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have beta-1,3-galactanase activity. In one aspect, the polypeptides differ by up to 10 amino acids, e.g., 1, 2, 3, 4, 5, 6, 7, 8, 9, or 10, from the mature polypeptide of SEQ ID NO: 2.

Preferably, the polypeptide has been isolated.

A polypeptide of the present invention preferably comprises or consists of the amino acid sequence of SEQ ID NO: 2 or an allelic variant thereof; or is a fragment thereof having beta-1,3-galactanase activity. In another aspect, the polypeptide comprises or consists of the mature polypeptide of SEQ ID NO: 2. In another aspect, the polypeptide comprises or consists of amino acids 21 to 256 of SEQ ID NO: 2.

In another embodiment, the present invention relates to a polypeptide, preferably an isolated polypeptide, having beta-1,3-galactanase activity encoded by a polynucleotide that hybridizes under very low stringency conditions, low stringency conditions, medium stringency conditions, medium-high stringency conditions, high stringency conditions, or very high stringency conditions with the mature polypeptide coding sequence of SEQ ID NO: 1 or the full-length complement hereof (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding polypeptides having beta-1,3-galactanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having beta-1,3-galactanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to a polypeptide, preferably an isolated polypeptide, having beta-1,3-galactanase activity encoded by a polynucleotide having a sequence identity to the mature polypeptide coding sequence of SEQ ID NO: 1 of at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for beta-1,3-galactanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having [Enzyme] Activity

A polypeptide having beta-1,3-galactanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alter-*

*naria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielevia achromatica, Thielevia albomyces, Thielevia albopilosa, Thielevia australeinsis, Thielevia fimeti, Thielevia microspora, Thielevia ovispora, Thielevia peruviana, Thielevia setosa, Thielevia spededonium, Thielevia subthermophila, Thielavia terrestris, Trichoderma harzianum, Trichoderma koningii, Trichoderma longibrachiatum, Trichoderma reesei*, or *Trichoderma viride* polypeptide.

In a preferred aspect, the polypeptide is an *Auricularia* polypeptide, e.g., an *Auricularia delicate* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned, e.g., from a strain of *Auricularia*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The host cell may be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and*

*Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is an *Auricularia* cell. In another aspect, the cell is an *Auricularia delicate* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Beta-1,3-galactanase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially beta-1,3-galactanase-free product are of particular interest in the production of eukaryotic polypeptides, in particular fungal proteins such as enzymes. The beta-1,3-galactanase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from beta-1,3-galactanase activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the beta-1,3-galactanase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention also relates to use of a polypeptide of the invention in coffee extraction.

The present invention also relates to a method for producing a coffee extract, comprising the steps:
a. providing roast and ground coffee beans;
b. adding to said coffee beans water and a polypeptide of the invention having beta-1,3-galactanase activity;
c. incubating to make an aqueous coffee extract; and
d. separating the coffee extract from the extracted coffee beans.

Signal Peptide and Propeptide

The present invention also relates to an isolated polynucleotide encoding a signal peptide comprising or consisting of amino acids 1 to 20 of SEQ ID NO: 2. The polynucleotides may further comprise a gene encoding a protein, which is operably linked to the signal peptide. The protein is preferably foreign to the signal peptide. In one aspect, the polynucleotide encoding the signal peptide is nucleotides 1 to 60 of SEQ ID NO: 1.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

Preferred Embodiments

1. A polypeptide having beta-1,3-galactanase activity, selected from the group consisting of:
    (a) a polypeptide having at least 65% sequence identity to the mature polypeptide of SEQ ID NO: 2;
    (b) a polypeptide encoded by a polynucleotide that hybridizes under low stringency conditions with the mature polypeptide coding sequence of SEQ ID NO: 1 or the full-length complement hereof;
    (c) a polypeptide encoded by a polynucleotide having at least 65% sequence identity to the mature polypeptide coding sequence of SEQ ID NO: 1;
    (d) a variant of the mature polypeptide of SEQ ID NO: 2 comprising a substitution, deletion, and/or insertion at one or more positions; and
    (e) a fragment of the polypeptide of (a), (b), (c), or (d) that has beta-1,3-galactanase activity.

2. The polypeptide of embodiment 1, which is an isolated polypeptide.

3. The polypeptide of embodiment 1 or 2, having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

4. The polypeptide of any of embodiments 1-3, which is encoded by a polynucleotide that hybridizes under low stringency conditions, low-medium stringency conditions, medium stringency conditions, medium-high stringency conditions, high stringency conditions, or very high stringency conditions with the mature polypeptide coding sequence of SEQ ID NO: 1 or the full-length complement hereof.

5. The polypeptide of any of embodiments 1-4, which is encoded by a polynucleotide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1.

6. The polypeptide of any of embodiments 1-5, comprising or consisting of SEQ ID NO: 2 or the mature polypeptide of SEQ ID NO: 2.

7. The polypeptide of any of embodiments 1-6, wherein the mature polypeptide is amino acids 21 to 256 of SEQ ID NO: 2.

8. The polypeptide of any of embodiments 1-7, which is a variant of the mature polypeptide of SEQ ID NO: 2 comprising a substitution, deletion, and/or insertion at one or more positions.

9. The polypeptide of embodiment 1, which is a fragment of SEQ ID NO: 2, wherein the fragment has beta-1,3-galactanase activity.

10. A composition comprising the polypeptide of any of embodiments 1-9.

11. Use of the polypeptide of any of embodiments 1-9 in coffee extraction.

12. An isolated polynucleotide encoding the polypeptide of any of embodiments 1-9.

13. A nucleic acid construct or expression vector comprising the polynucleotide of embodiment 12 operably linked to one or more control sequences that direct the production of the polypeptide in an expression host.

14. A recombinant host cell comprising the polynucleotide of embodiment 12 operably linked to one or more control sequences that direct the production of the polypeptide.

15. A method of producing the polypeptide of any of embodiments 1-9, comprising cultivating a cell, which in its wild-type form produces the polypeptide, under conditions conducive for production of the polypeptide.

16. The method of embodiment 15, further comprising recovering the polypeptide.

17. A method of producing a polypeptide having beta-1,3-galactanase activity, comprising cultivating the host cell of embodiment 14 under conditions conducive for production of the polypeptide.

18. The method of embodiment 17, further comprising recovering the polypeptide.

19. A transgenic plant, plant part or plant cell transformed with a polynucleotide encoding the polypeptide of any of embodiments 1-9.

20. A method of producing a polypeptide having beta-1,3-galactanase activity, comprising cultivating the transgenic plant or plant cell of embodiment 19 under conditions conducive for production of the polypeptide.

21. The method of embodiment 20, further comprising recovering the polypeptide.

22. A method of producing a mutant of a parent cell, comprising inactivating a polynucleotide encoding the polypeptide of any of embodiments 1-9, which results in the mutant producing less of the polypeptide than the parent cell.

23. A mutant cell produced by the method of embodiment 22.

24. The mutant cell of embodiment 23, further comprising a gene encoding a native or heterologous protein.

25. A method of producing a protein, comprising cultivating the mutant cell of embodiment 23 or 24 under conditions conducive for production of the protein.

26. The method of embodiment 25, further comprising recovering the protein.

27. An isolated polynucleotide encoding a signal peptide comprising or consisting of amino acids 1 to 20 of SEQ ID NO: 2.

28. A nucleic acid construct or expression vector comprising a gene encoding a protein operably linked to the polynucleotide of embodiment 27, wherein the gene is foreign to the polynucleotide encoding the signal peptide.

29. A recombinant host cell comprising a gene encoding a protein operably linked to the polynucleotide of embodiment 27, wherein the gene is foreign to the polynucleotide encoding the signal peptide.

30. A method of producing a protein, comprising cultivating a recombinant host cell comprising a gene encoding a protein operably linked to the polynucleotide of embodiment 27, wherein the gene is foreign to the polynucleotide encoding the signal peptide, under conditions conducive for production of the protein.

31. The method of embodiment 30, further comprising recovering the protein.

32. A whole broth formulation or cell culture composition comprising a polypeptide of any of embodiments 1-9.

EXAMPLES

Materials

Chemicals used as buffers and substrates were commercial products of at least reagent grade.

Media and Solutions

YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter. The medium was sterilized by autoclaving at 15 psi for 15 minutes (Bacteriological Analytical Manual, 8th Edition, Revision A, 1998).

COVE sucrose plates were composed of 342 g Sucrose (Sigma S-9378), 20 g Agar powder, 20 ml Cove salt solution (26 g $MgSO_4.7H_2O$, 26 g KCL, 26 g $KH_2PO_4$, 50 ml Cove trace metal solution) and deionized water to 1 liter), and deionized water to 1 liter). The medium was sterilized by autoclaving at 15 psi for 15 minutes (Bacteriological Analytical Manual, 8th Edition, Revision A, 1998). The medium was cooled to 60° C. and added 10 mM acetamide, 15 mM CsCl, Triton X-100 (50 µl/500 ml)).

Cove trace metal solution was composed of 0.04 g $Na_2B_4O_7.10H_2O$, 0.4 g $CuSO_4.5H_2O$, 1.2 g $FeSO_4.7H_2O$, 0.7 g $MnSO_4.H_2O$, 0.8 g $Na_2MoO_4.2H_2O$, 10 g $ZnSO_4.7H_2O$, and deionized water to 1 liter.

Example 1: Construction of an *Aspergillus oryzae* Expression Vector Containing *Auricularia Delicata* cDNA Sequence Encoding a Family GH16 Polypeptide Having Endo-β-1,3-Galactanase Activity The assembly of the genome of *Auricularia delicata* SS-5 (DOE Joint Genome Institute, Walnut Creek, Calif. 94598, USA) were retrieved from NCBI, Bethesda Md., USA, together with corresponding gene models and used as a starting point for detecting GH16 homologues in the genome. More precise gene models were constructed manually using multiple known GH16 protein sequences as a guide.

Based on the nucleotide sequence of the *Auricularia delicata* SS-5 genome sequence (DOE Joint Genome Institute, Walnut Creek, Calif. 94598, USA), a synthetic gene P24GUG (SEQ ID NO: 1) was obtained from GeneArt (Invitrogen, Carlsbad, Calif., USA) encoding the cDNA of the *Auricularia delicata* endo-beta-1,3-galactanase with additional BamHI and XhoI restriction sites to facilitate cloning into an expression vector.

The GeneArt construct containing P24GUG was treated with BamHI and XhoI restriction enzymes and the reaction products were isolated by 1.0% agarose gel electrophoresis using 40 mM Tris base, 20 mM sodium acetate, 1 mM disodium EDTA (TAE) buffer where a 780 bp product band was excised from the gel and purified using an illustra GFX® PCR DNA and Gel Band Purification Kit (GE Healthcare Life Sciences, Brondby, Denmark) according to the manufacturer's instructions. The fragment was then cloned by ligation into Bam HI and Xho I digested pDau109 using T4 DNA ligase (Roche Diagnostics NS, Hvidovre, Denmark) according to the manufacturer's instructions resulting in plasmid pP24GUG. Cloning of the P24GUG gene into Bam HI-Xho I digested pDau109 resulted in the transcription of the *Auricularia delicata* P24GUG gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The ligated plasmid pP24GUG was transformed into One Shot® TOP10F" Chemically Competent *E. coli* cells (Invitrogen, Carlsbad, Calif., USA) according to the manufacturer's protocol and plated onto LB plates supplemented with 0.1 mg of ampicillin per ml. After incubating at 37° C. overnight, colonies were seen growing under selection on the LB ampicillin plates. Two colonies transformed with the P24GUG GH16 construct were cultivated in LB medium supplemented with 0.1 mg of ampicillin per ml and plasmid was isolated with a QIAprep Spin Miniprep Kit (QIAGEN Inc., Valencia, Calif., USA) according to the manufacturer's protocol.

Isolated plasmids were sequenced with vector primers and P24GUG gene specific primers in order to determine a representative plasmid expression clone that was free of errors.

Example 2: Characterization of the *Auricularia delicata* cDNA Sequence Encoding a GH16 Polypeptide Having Endo-β-1,3-Galactanase Activity DNA sequencing of the *Auricularia delicata* P24GUG GH16 cDNA clone was performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence and deduced amino acid sequence of the *Auricularia delicata* P24GUG gene is shown in SEQ ID NO: 1 and SEQ ID NO: 2, respectively. The coding sequence is 771 bp including the stop codon. The encoded predicted protein is 256 amino acids. Using the SignalP program (Nielsen et al., 1997, *Protein Engineering* 10: 1-6), a signal peptide of 20 residues was predicted. The predicted mature protein contains 236 amino acids with a predicted molecular mass of 26 kDa and an isoelectric pH of 7.3.

Example 3: Expression of the *Auricularia delicata* GH16 Endo-β-1,3-Galactanase The expression plasmid pP24GUG was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Auricularia delicata* GH16 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, Calif., USA) by Coomassie staining. One transformant was selected for further work and designated *Aspergillus oryzae* 99.1.

For larger scale production, *Aspergillus oryzae* 99.1 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 µm PES filter (Thermo Fisher Scientific, Roskilde, Denmark). Fresh culture broth from this transformant produced a band of GH16 protein of approximately 26 kDa. The identity of the band as the *Auricularia delicata* GH16 polypeptide was verified by peptide sequencing.

Example 4: Purification of the *Auricularia delicata* Endo-β-1,3-Galactanase The harvested cell culture broth of *Auricularia delicata* was supplemented with ammonium sulphate to a final concentration of 2 M and pH was adjusted to 7.5. The sample was then loaded on a hydrophobic column (packed bed of butyl Toyo pearl; gradient: 0-100% B in 10 column volumes; buffer A: 50 mM Mes and 2 M ammonium sulphate; buffer B: 50 mM Mes). SDS-PAGE (reducing conditions) confirmed that the galactanase was not eluted through the column in the flow-through or wash fraction. Based on the SDS-PAGE, fractions containing proteins of the expected Mw of 27.7 kDa (fractions 30-50) were pooled, concentrated and buffer-exchanged into 20 mM sodium acetate buffer pH 6.5 by centrifugation in viva spin column 3 kDa MWCO membrane (3000×g spin centrifugation).

Enzymes

In the examples below the following galactanase enzymes were used:

| Enzyme | Description | Origin | Sequence | GH |
|---|---|---|---|---|
| GALACTANASE1 | Endo-β-1,3-galactanase | Auricularia delicata | SEQ ID NO: 2 | GH16 |
| GALACTANASE2 | Endo-β-1,3-galactanase | Magnaporthe oryzae | SWISSPROT: A4QYM3 | GH16 |
| GALACTANASE3 | Endo-β-1,3-galactanase | Neurospora Crassa | UNIPROT: Q7RZX8 | GH16 |
| GALACTANASE4 | Exo-β-1,3-galactanase | Irpex lacteus | UNIPROT: B9ZZS1 | GH43 |

Example 5: Synthesis of β-1,3-Galactan Substrates

Different carbohydrates were used as substrates for characterizing the β-1,3-galactanases:

a) Gum Arabic

Commercially available (Merck). Complex polysaccharide composed of D-galactose (44%); L-arabinose (24%); D-glucuronic acid (14.5%); L-rhamnose (13%); 4-O-methyl-D-glucuronic acid (1.5%). β-1,3-linked galactoses form the backbone.

b) Acid Treated Gum Arabic

Gum Arabic was treated with 0.1 M TFA for 1 h at 90° C. The reaction was stopped by adjusting the pH to 7 with 4 M NaOH. The sample was then reduced by NaBH$_4$ (2 mg per mg of polysaccharide) for 3 h at room temperature followed by dialysis overnight. The solid was recovered by freeze drying. TLC confirmed the decrease of arabinose in the polysaccharide.

c) Smith Degraded Gum Arabic

Gum Arabic was degraded according to the Smith degradation method described in the literature (Tsumuraya et al., Carbohydrate Research, 1984, 134, 215-228). Gum Arabic side chains (arabinose and β-1,6-linked galactose) were first cleaved by periodate (excess destroyed by ethylene glycol) then reduced by sodium borohydride, and hydrolysed with dilute acid under mild conditions. The procedure was repeated 3 times. NMR confirmed the decrease of arabinose and β-1,6-linked galactoses from the side chains. The oxidation of Gum Arabic (up to 5 g) with 50 mM sodium metaperiodate (up to 500 mL) was carried out in the dark at 4° C. for 48-96 h. The reaction was terminated by addition of ethylene glycol (up to 4 mL) and stirring for 2 h at room temperature. After overnight dialysis (3.5 kDa MWCO, distilled water), reduction of the oxidised product was performed with NaBH$_4$ (2 mg per mg of polysaccharide) for 3 h. The reaction was terminated by making pH 7 with 10% AcOH and dialysing overnight. After evaporating to a small volume, the sample was hydrolysed with diluted TFA (0.5 M) under mild conditions for 24 h at room temperature. After evaporating most of the acid and adjusting the pH to 7 by addition of 1 M NaOH, the substrate was precipitated with 3 volumes of ethanol and recovered by centrifugation and freeze drying. The procedure was repeated 3 times to produce triple Smith degraded Gum Arabic.

Example 6: Reducing Sugar Assay (PAH-BAH Assay) for Quantification of β-1,3-Galactanase Activity β-1,3-Galactanase activity was determined in two steps. The first step is an enzymatic step where carbohydrate substrates are hydrolysed by the catalytic action of the galactanase. The second step is a non-enzymatic detection step where the aldehyde group of the mono- and oligosaccharides are reduced to form a yellow coloured compound.

a) Activity Assay—Degradation of Polysaccharides

50 μL of a 0.08 g/L enzyme solution (MilliQ water for blank sample) was mixed with 50 μL of Activity buffer (20 mM sodium acetate buffer pH 5) and 50 μL of Substrate solution (5-10 g/L dissolved in MilliQ water) in a 96-well PCR-MTP The reaction was carried out at 40° C. for 45 minutes in a PCR machine The reaction was stopped by increasing the temperature to 95° C. for 10 minutes b) Activity Assay—Detection of Reducing Sugars (PAH-BAH—Assay)

25 μL sample from above was diluted with 100 μL 1 M NaOH in a new 96-well PCR-MTP 75 μL of a fresh stop solution was added into the well (4-hydroxy benzoic acid hydrazide dissolved in 15 g/L in 2% (w/v) NaOH and 5% (w/v) K—Na-tartrate)

Reaction was incubated 10 minutes at 70° C.

Endpoint absorbance was measured at 405 nm

Activity Calculation:

A standard curve for reducing sugars was made with different galactose concentrations ranging from 0.05 g/L to 3 g/L following the procedure above. The following standard equation was obtained: amount of sugar released (measured as μg of galactose equivalents): $m_{gal\ eq}=(A_{405}-0.0061)/0.016$. The observed absorbance of the blank was always subtracted from the obtained absorbance allowing comparison of all the results. The quantity of reducing sugars released after reaction (45 minutes at 40° C.) was calculated according to the standard curve. The enzymatic activity (%) was calculated as the percentage of released galactose equivalents compared to the total mass of the polysaccharide substrate (Table 1).

Example: For an assay with 5 g/L Smith degraded Gum Arabic, the total amount of polysaccharide is 250 μg. After the two-step reaction, a sample absorbance of 2.26 with a blank absorbance of 0.16 corresponds to 131 μg of galactose equivalents giving an observed activity of 52%.

TABLE 1

Relative activity (% galactose reducing end equivalents released per mass of substrate) for degrading Gum arabic and related products

| Enzymes | Smith degraded Gum Arabic | Acid treated Gum Arabic | Gum Arabic |
|---|---|---|---|
| GALACTANASE1 | 52.7 | 9.2 | 2.6 |
| GALACTANASE2 | 43.6 | 0.5 | 0.2 |
| GALACTANASE3 | 46.2 | 9.3 | 2.7 |
| GALACTANASE4 | 25.6 | 17.7 | 2.4 |

The decrease of side chains on the substrate increases the galactanase activity.

Example 7: TLC Assay for Detection of β-1,3-Galactanase Activity

The heat inactivated reaction mixture (Example 6a) was analysed by TLC (Silica gel 60 F254) to characterize the enzymes with regards to endo and exo activity. The eluent was butan-1-ol, ethanol and water (5/5/4 v/v). Reference compounds were arabinose ($Rf_{ara}$=0.56); galactose ($Rf_{Gal}$=0.53); β-1,4-galactobiose ($Rf_{Gal2}$=0.50) and β-1,6-galactotetraose ($Rf_{Gal4}$=0.44). The expected reaction product β-1,3-galactobiose was expected to migrate with similar Rf as β-1,4-galactobiose, and β-1,3-galactotetraose was assumed to migrate with similar Rf as β-1,6-galactotetraose. Results are shown in Table 2.

TABLE 2

Relative activity (% galactose reducing end equivalents released per mass of substrate) and product composition for degradation of β-1,3-Galactan (triple Smith degraded Gum Arabic) by 4 galactanases

| | Smith degraded Gum Arabic | | | |
| --- | --- | --- | --- | --- |
| Enzymes | GALACTANASE1 | GALACTANASE2 | GALACTANASE3 | GALACTANASE4 |
| % Activity | 52.7 | 43.6 | 46.2 | 25.6 |
| Arabinose | − | − | − | − |
| Galactose | ++ | ++ | ++ | +++ |
| Galactobiose | +++ | +++ | +++ | + |
| Galactotetraose | ++ | ++ | ++ | − |

The release of arabinose, galactose, galactobiose and galactotetraose was detected by TLC. (−) means no spot on the plate, and (+), (++), (+++) indicate a spot with different intensity (the more +, the more intense the spot). The product composition justifies primarily endo activity of GALACTANASE1, GALACTANASE2 and GALACTANASE3 and exo activity of GALACTANASE4.

Example 8: pH Optima and pH Stability of Galactanases pH stability of GALACTANASE1 and GALACTANASE4 (0.08 g/L) was evaluated by determining the enzymatic activity by the reducing sugar assay (Example 6) after incubation with a substrate solution (2.5 g/L Smith degraded Gum Arabic or 15 g/L acid treated Gum Arabic) for 45 minutes at 40° C. at selected pH values in the interval 1.5-10. The activity of the galactanases was tested right after adjusting the pH (t0), or after incubating the enzyme at the given pH for 24 h in the fridge before addition of the substrate (24 h) (Tables 3 and 4). The pH was measured before and after reaction to confirm that the pH was constant during the incubation.

TABLE 3

Activity buffer composition, pH was adjusted according to the wanted pH

| pH | Employed buffer |
| --- | --- |
| 1.5; 2; 2.5 | 60 mM KCl/HCl |
| 3; 3.6; 3.9; 4.3; 4.7; 5; 5.2; 5.7 | 20 mM Sodium acetate |
| 6 | 50 mM Mes |
| 7 and 8 | 50 mM HEPES |
| 9 and 10 | 50 mM Tris HCl |

TABLE 4

Observed activity (%) at different pH values

| | Activity GALACTANASE1 | | | Activity GALACTANASE4 | | |
| --- | --- | --- | --- | --- | --- | --- |
| | Smith degraded Gum Arabic | | Acid treated Gum Arabic | Smith degrade Gum Arabic | | Acid treated Gum Arabic |
| Substrate pH | t 0 | 24 h | t 0 | t 0 | 24 h | t 0 |
| 1.5 | 0.9 | 0.0 | 0.0 | 0.5 | 0.0 | 0.0 |
| 2 | 27.4 | 1.5 | 2.3 | 1.6 | 0.6 | 1.8 |

TABLE 4-continued

Observed activity (%) at different pH values

| | Activity GALACTANASE1 | | | Activity GALACTANASE4 | | |
| --- | --- | --- | --- | --- | --- | --- |
| | Smith degraded Gum Arabic | | Acid treated Gum Arabic | Smith degrade Gum Arabic | | Acid treated Gum Arabic |
| Substrate pH | t 0 | 24 h | t 0 | t 0 | 24 h | t 0 |
| 2.5 | 40.2 | 31.4 | 2.6 | 6.1 | 2.0 | 8.8 |
| 3 | 42.5 | 32.9 | 6.8 | 13.6 | 8.3 | 17.1 |
| 3.6 | 42.6 | 27.2 | 10.0 | 19.1 | 8.5 | 18.3 |
| 3.9 | 44.5 | 37.6 | 10.2 | 19.2 | 9.4 | 18.0 |
| 4.3 | 40.9 | 45.1 | 9.7 | 19.5 | 9.4 | 17.2 |
| 4.6 | 43.6 | 43.0 | 9.5 | 18.8 | 8.0 | 16.4 |
| 5.1 | 45.7 | 38.4 | 8.3 | 19.3 | 8.3 | 13.9 |
| 5.7 | 40.8 | 36.9 | 7.5 | 16.6 | 8.6 | 9.1 |
| 6 | 39.4 | 40.7 | 6.8 | 15.2 | 8.2 | 8.6 |
| 7 | 36.3 | 39.8 | 3.3 | 9.5 | 4.5 | 2.1 |
| 8 | 19.1 | 20.9 | 0.2 | 0.5 | 0.1 | 0.0 |
| 9 | 2.6 | 2.3 | 0.0 | 0.8 | 0.2 | 0.0 |
| 10 | 0.0 | 0.5 | 0.0 | 0.4 | 0.1 | 0.0 |

Example 9: Thermostability of Galactanases Evaluated by DSC

Thermostabilities of GALACTANASE1, GALACTANASE2, GALACTANASE3 and GALACTANASE4 were evaluated by Differential Scanning calorimetry (DSC) in the appropriate buffer solution (20 mM Sodium acetate pH 6.5). The temperature corresponding to the apex of the peak in the thermogram was noted as the thermal transition midpoint ($T_m$ (° C.)) for the enzymes.

TABLE 5

Midpoint temperatures

| Enzyme | Temperature °C. |
|---|---|
| GALACTANASE1 | 66.2 |
| GALACTANASE2 | 58.0 |
| GALACTANASE3 | 62.3 |
| GALACTANASE4 | 43.1 |

Example 10: Thermostability of Galactanases Evaluated by Reducing Sugar Assay at Different Temperatures Thermostabilities of GALACTANASE1 and GALACTANASE4 (0.04 g/L) were evaluated by determining the enzymatic activity by the reducing sugar assay (Example 6) after incubation with 2.5 g/L substrate solution (Smith degraded Gum Arabic) for 45 minutes at pH 5 at selected temperatures in the interval 20° C.-90° C. The enzyme was added to the assay after the sample (buffer and substrate solution) was heated to the selected temperature. Temperature optima of 60° C. (GALACTANASE1) and 30° C. (GALACTANASE4) were observed (Table 6).

TABLE 6

Observed activity (%) at different temperatures

| Temperature (° C.) | Activity GALACTANASE1 | Activity GALACTANASE4 |
|---|---|---|
| 20 | 44.1 | 19.9 |
| 30 | 42.9 | 20.2 |
| 40 | 41.5 | 20.2 |
| 50 | 38.0 | 18.5 |
| 60 | 50.1 | 16.6 |
| 70 | 44.8 | 13.4 |
| 80 | 47.9 | 4.5 |
| 90 | 17.3 | 0.3 |

Example 11: Activity Assay of *Auricularia* Delicate Galactanase on Coffee

Principle:

Galactanase activity was determined in two steps. The first step is an enzymatic step where the coffee is hydrolysed by the catalytic action of the galactanase. The second step is a detection step where the enzymatic activity is measured by different methods.

Substrate:

Coffee brew of spent defatted *Arabica* Coffee bean was used for the assays. The main polysaccharides of coffee brew and roasted coffee are galactomannans and arabinogalactans. Galactomannans are polysaccharides composed of a linear β-1,4-mannopyranosyl backbone substituted with O-6 arabinose and galactose residues. Arabinogalactans are polysaccharides composed of a linear β-1,3-galactopyranosyl backbone substituted with O-6 arabinose and galactose residues.

Activity Assay: Solubilisation of Defatted *Arabica* Coffee
  320 μL of coffee brew was mixed with 30 μL of a 0.16 g/L enzyme solution (MilliQ water for blank)
  The sample was incubated 2 h or 24 h at 40° C. at the pH of the coffee.
  The reaction was stopped by increasing the temperature to 95° C. for 10 minutes
  The sample was centrifuged 5 minutes at 10 000 rpm
Quantification:
  Activity by measurement of direct coloration ($A_{361}$): 25 μL of supernatant from Activity assay was mixed with 225 μL of a 0.2 M $Na_2CO_3$ solution and endpoint absorbance was measured at 361 nm.
  Monosaccharide release: 100 μL of supernatant from Activity assay was mixed with 100 μL of 4 M TFA for 2 h at 96° C. The sample was diluted 10 times with a 0.2 M NaOH solution and then another 10 times with a 5 mM NaOH solution. Analysis of released monosaccharides was carried out by HPLC.
Dry Matter Assay:
  1400 μL of coffee brew was mixed with 100 μL of a 0.16 g/L enzyme solution (MilliQ water for blank)
  The sample was incubated 2 h at 40° C. and coffee pH.
  The reaction was stopped by increasing the temperature up to 95° C. for 10 minutes
  The sample was centrifuged 5 minutes at 10 000 rpm
  The supernatant was weighed and transferred to a new eppendorf tube
  The sample was dried overnight in a 110° C. heating cupboard
  The dry residue was weighed and the released dry matter was calculated in % of total dry weight of the coffee solution

TABLE 7

Dry matter (%), activity by direct coloration and monosaccharide composition after 2 h reaction at coffee pH:

| Enzyme | Dry matter (%) | Direct coloration ($A_{361}$) | Monosaccharide concentration (g/L) | | |
|---|---|---|---|---|---|
| | | | Arabinose | Galactos | Mannose |
| GALACTANASE1 | 7.1 | 5.80 | 7 | 30 | 4 |
| GALACTANASE2 | 2.6 | 1.62 | 1 | 5 | 3 |
| GALACTANASE3 | 3.9 | 2.73 | 4 | 17 | 4 |
| Blank | 1.1 | — | 0.4 | 1.2 | 3.2 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method or producing a coffee extract, comprising the steps:
   (a) providing roast and ground coffee beans;
   (b) adding water and a polypeptide having beta-1,3-galactanase activity to the coffee beans, wherein the polypeptide has at least 90% sequence identity to the mature polypeptide of SEQ ID NO: 2;
   (c) incubating to make an aqueous coffee extract; and
   (d) separating the coffee extract from the extracted coffee beans.

2. The method of claim 1, wherein the polypeptide has at least 97% sequence identity to the mature polypeptide of SEQ ID NO: 2.

3. The method of claim 1, wherein the polypeptide is the mature polypeptide of SEQ ID NO: 2.

4. The method of claim 1, wherein the polypeptide has one or more amino acids absent from the amino and/or carboxyl terminus of the mature polypeptide of SEQ ID NO: 2.

5. The method of claim 1, wherein the polypeptide is encoded by a polynucleotide having at least 95% sequence identity to the mature polypeptide coding sequence of SEQ ID NO: 1.

6. The method of claim 1, wherein the polypeptide is a variant of the mature polypeptide of SEQ ID NO: 2 comprising a substitution, deletion, and/or insertion at one or more positions.

* * * * *

SEQUENCE LISTING

<160> NUMBER OF SEQ ID NOS: 2

<210> SEQ ID NO 1

<211> LENGTH: 771
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(768)

<400> SEQUENCE: 1

```
atg att tcc gtc gct ttg gtc cca ctc ttc atc gct gtg ctt gcc agc      48
Met Ile Ser Val Ala Leu Val Pro Leu Phe Ile Ala Val Leu Ala Ser
1               5                   10                  15 gcg acg tcg agc gtc gtc ctc ccg acg aac tcg ttc agc tcg tac agc      96
Ala Thr Ser Ser Val Val Leu Pro Thr Asn Ser Phe Ser Ser Tyr Ser
            20                  25                  30 gcc ttt gag cag cac tgg aac tac ctc tac cct tgg ggc tcg gac cac     144
Ala Phe Glu Gln His Trp Asn Tyr Leu Tyr Pro Trp Gly Ser Asp His
        35                  40                  45 aac ggc tcc ggg cgc atg gtg ggc agc tcg tcg aac cac acg tac atc     192
Asn Gly Ser Gly Arg Met Val Gly Ser Ser Asn His Thr Tyr Ile
    50                  55                  60 agc gtc gcg gac aac gtt ctc acg ctc acc tcg aag ccc gtc tcc ggg     240
Ser Val Ala Asp Asn Val Leu Thr Leu Thr Ser Lys Pro Val Ser Gly
65                  70                  75                  80 cag cct ccg agc acc tcc aac ccg cac ccg gcc atc cat tac ttc tct     288
Gln Pro Pro Ser Thr Ser Asn Pro His Pro Ala Ile His Tyr Phe Ser
                85                  90                  95 ggc act gtc cat gcg aag caa cag gtc aag gtc gac gga agt agc gtc     336
Gly Thr Val His Ala Lys Gln Gln Val Lys Val Asp Gly Ser Ser Val
            100                 105                 110 acg ggg ttc gac atc cag gga gag ttc att gct ccg act gca aaa ggc     384
Thr Gly Phe Asp Ile Gln Gly Glu Phe Ile Ala Pro Thr Ala Lys Gly
        115                 120                 125 acg tgg cct gcg ttc tgg ctt act gcg gtg aat gga tgg cct ccg gag     432
Thr Trp Pro Ala Phe Trp Leu Thr Ala Val Asn Gly Trp Pro Pro Glu
    130                 135                 140 agc gac att ggt gaa tgg aag ggc acc cag gaa aac tgg ttc aat acc     480
Ser Asp Ile Gly Glu Trp Lys Gly Thr Gln Glu Asn Trp Phe Asn Thr
145                 150                 155                 160 ttc aac act tcc tca tca gtc gcg acg aag cgc gtc gcc tgg ccc acg     528
Phe Asn Thr Ser Ser Ser Val Ala Thr Lys Arg Val Ala Trp Pro Thr
                165                 170                 175 gac ggc cag ttc cat tcc ctg aag gcc gag ctg cgc acg atc tcg ggc     576
Asp Gly Gln Phe His Ser Leu Lys Ala Glu Leu Arg Thr Ile Ser Gly
            180                 185                 190 aac acg aag gac ctc tcg atc aag tac tac ttc gac gga acg ctg cag     624
Asn Thr Lys Asp Leu Ser Ile Lys Tyr Tyr Phe Asp Gly Thr Leu Gln
        195                 200                 205 gcg act cac acg gca gct aac ttc cgc aac gcc gct atg tgg ttg att     672
Ala Thr His Thr Ala Ala Asn Phe Arg Asn Ala Ala Met Trp Leu Ile
    210                 215                 220 gtc gac ctt cag atg gag gga agc tcg ggc tct ccg ggc cca gct ggc     720
Val Asp Leu Gln Met Glu Gly Ser Ser Gly Ser Pro Gly Pro Ala Gly
225                 230                 235                 240 ggc acg acg ttc caa atc agg aac gtc cag ttg acg aag tat acg ccg     768
Gly Thr Thr Phe Gln Ile Arg Asn Val Gln Leu Thr Lys Tyr Thr Pro
                245                 250                 255 tga                                                                  771
```

<210> SEQ ID NO 2

```
<211> LENGTH: 256
<212> TYPE: PRT
<213> ORGANISM: Artificial Sequence
<220> FEATURE:
<223> OTHER INFORMATION: Synthetic Construct

<400> SEQUENCE: 2

Met Ile Ser Val Ala Leu Val Pro Leu Phe Ile Ala Val Leu Ala Ser
1               5                   10                  15

Ala Thr Ser Ser Val Val Leu Pro Thr Asn Ser Phe Ser Ser Tyr Ser
            20                  25                  30

Ala Phe Glu Gln His Trp Asn Tyr Leu Tyr Pro Trp Gly Ser Asp His
        35                  40                  45

Asn Gly Ser Gly Arg Met Val Gly Ser Ser Ser Asn His Thr Tyr Ile
    50                  55                  60

Ser Val Ala Asp Asn Val Leu Thr Leu Thr Ser Lys Pro Val Ser Gly
65                  70                  75                  80

Gln Pro Pro Ser Thr Ser Asn Pro His Pro Ala Ile His Tyr Phe Ser
                85                  90                  95

Gly Thr Val His Ala Lys Gln Gln Val Lys Val Asp Gly Ser Ser Val
                100                 105                 110

Thr Gly Phe Asp Ile Gln Gly Glu Phe Ile Ala Pro Thr Ala Lys Gly
            115                 120                 125

Thr Trp Pro Ala Phe Trp Leu Thr Ala Val Asn Gly Trp Pro Pro Glu
        130                 135                 140

Ser Asp Ile Gly Glu Trp Lys Gly Thr Gln Glu Asn Trp Phe Asn Thr
145                 150                 155                 160

Phe Asn Thr Ser Ser Ser Val Ala Thr Lys Arg Val Ala Trp Pro Thr
                165                 170                 175

Asp Gly Gln Phe His Ser Leu Lys Ala Glu Leu Arg Thr Ile Ser Gly
            180                 185                 190

Asn Thr Lys Asp Leu Ser Ile Lys Tyr Tyr Phe Asp Gly Thr Leu Gln
        195                 200                 205

Ala Thr His Thr Ala Ala Asn Phe Arg Asn Ala Ala Met Trp Leu Ile
    210                 215                 220

Val Asp Leu Gln Met Glu Gly Ser Ser Gly Ser Pro Gly Pro Ala Gly
225                 230                 235                 240

Gly Thr Thr Phe Gln Ile Arg Asn Val Gln Leu Thr Lys Tyr Thr Pro
                245                 250                 255
```